United States Patent
Hachmann et al.

[11] Patent Number: 5,646,105
[45] Date of Patent: Jul. 8, 1997

[54] CLEANING DISINFECTANT

[75] Inventors: Klaus Hachmann, Hilden; Carsten Friese, Hamburg, both of Germany

[73] Assignee: Henkel Ecolab GmbH & Co., Duesseldorf, Germany

[21] Appl. No.: 411,715

[22] PCT Filed: Sep. 30, 1993

[86] PCT No.: PCT/EP93/02670

§ 371 Date: May 4, 1995

§ 102(e) Date: May 4, 1995

[87] PCT Pub. No.: WO94/09105

PCT Pub. Date: Apr. 28, 1994

[30] Foreign Application Priority Data

Oct. 9, 1992 [DE] Germany .................. 42 34 070.5

[51] Int. Cl.$^6$ .................. C11D 7/32; C11D 7/50
[52] U.S. Cl. .................. 510/382; 510/422; 510/427; 510/432; 510/499
[58] Field of Search .................. 252/546, 153, 252/106; 510/382, 422, 427, 432, 499

[56] References Cited

U.S. PATENT DOCUMENTS

| | | | |
|---|---|---|---|
| 4,396,521 | 8/1983 | Borrello | 252/118 |
| 4,652,585 | 3/1987 | Gerhardt et al. | 514/563 |
| 5,068,064 | 11/1991 | Proietto et al. | 260/404.5 |
| 5,185,145 | 2/1993 | Eggensperger et al. | 424/78.08 |
| 5,393,789 | 2/1995 | Eggensperger et al. | 514/674 |
| 5,403,505 | 4/1995 | Hachmann et al. | 252/106 |

FOREIGN PATENT DOCUMENTS

| | | |
|---|---|---|
| 2012288 | 9/1990 | Canada . |
| 0156275 | 10/1985 | European Pat. Off. . |
| 4005784 | 8/1991 | Germany . |
| 9113965 | 9/1991 | WIPO . |

*Primary Examiner*—Paul Lieberman
*Assistant Examiner*—Gregory R. Delcotto
*Attorney, Agent, or Firm*—Ernest G. Szoke; Wayne C. Jaeschke; Real J. Grandmaison

[57] ABSTRACT

A clear aqueous disinfectant compositon containing the reaction product of (a) an N-substituted propylenediamine corresponding to formula I:

$$R_1\text{—NH—CH}_2\text{—CH}_2\text{—CH}_2\text{—NH}_2 \quad \text{(I)}$$

in which $R_1$ is a linear alkyl radical containing 12 to 14 carbon atoms, and (b) a compound corresponding to formula II:

$$R_2\text{—O—CO—CH}_2\text{—CH}_2\text{—CH(NH}_2)\text{—COOH} \quad \text{(II)}$$

in which $R_2$ is a hydrogen atom or an alkyl radical containing 1 to 4 carbon atoms, in a molar ration of(a) to (b) of from about 1:1 to about 1:2, respectively, and further containing (c) a solubilizer selected from the group consisting of benzyl alcohol, 2-phenoxyethanol, 1-phenoxypropanol, and mixtures thereof.

14 Claims, No Drawings

CLEANING DISINFECTANT

BACKGROUND OF THE INVENTION

1. Field of the Invention
2. Discussion of Related Art

A cleaning disinfectant

This invention relates to a cleaning, water-containing disinfectant based on reaction products of a) N-substituted propylenediamines corresponding to formula I:

in which $R_1$ is a linear alkyl radical containing 12 to 14 carbon atoms, and b) compounds corresponding to formula II:

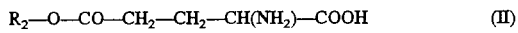

in which $R_2$ is a hydrogen atom or an alkyl radical containing 1 to 4 carbon atoms, the molar ratio of a) to b).being about 1:1 to about 1:2, (composition U) and/or salts thereof with inorganic or organic acids, optionally together with nonionic and/or amphoteric surfactants, complexing agents and organic solvents according to EP 156 275, characterized in that it contains benzyl and/or 2-phenoxyethanol and/or 1-phenoxypropanol as solubilizer.

The preparation and use of composition U are described in EP 156 275. Active-substance combinations containing U are known from WO 91/13965. However, it has been found that the solutions mentioned therein do not always dissolve clearly in water at room temperature either on its own or in conjunction with typical solvents, such as alcohols and glycol ethers, for example ethanol, propanol, isopropanol or butyl diglycol (diethylene glycol monobutyl ether) and separate into layers in the event of prolonged storage. This is attributable to the unfavorable temperature-dependent clear and cloud point of the solutions.

DESCRIPTION OF THE INVENTION

It has now been found that clear cleaning disinfectants can be obtained if, in addition to the usual solvents, benzyl alcohol and/or 2-phenoxyethanol and/or 1-phenoxypropanol is/are used as solubilizers for the composition U. A mixture of benzyl alcohol and 1-phenoxypropanol, more particularly in a quantity ratio of around 1:1, is preferably used.

The quantity of solubilizer in the disinfectant as a whole is about 3 to about 30% by weight and preferably about 7 to about 15% by weight. The ratio by weight of solubilizer to U is about 1.0:6.0 to 1.0:0.05 and preferably of the order of 1:0.5 to 1:0.07.

By using these alcohols as solubilizers, the clear point of the disinfectant solutions in typical solvents could be reduced to temperatures well below 20° C. They remained stable in storage over an observation period of around 6 months.

This favorable result remained intact even when nonionic surfactants, builders and optionally fragrances and/or corrosion inhibitors were added to the solutions.

The composition U is used in quantities of around 5 to 40% by weight and preferably in quantities of around 10 to 25% by weight.

If a cleaning effect is required in addition to the antimicrobial effect, the disinfectants may contain one or more surfactants, preferably from the groups of nonionic surfactants and amphoteric surfactants.

Suitable nonionic surfactants are, for example, alkyl polyglycosides preferably containing 8 to 22 carbon atoms in the alkyl radical, reaction products of 4 to 40 and preferably 4 to 20 mole equivalents of ethylene oxide (EO) and/or propylene oxide (PO) with fatty alcohols, fatty acids, fatty amines, fatty acid amides or alkane sulfonamides, of which the fatty alkyl radicals preferably contain 8 to 22 carbon atoms, and with alkylphenols. The end-capped derivatives of such alkoxylation products, preferably with terminal groups containing 2 to 10 carbon atoms, are also suitable. Addition products of 5 to 16 moles of ethylene oxide with cocofatty alcohols or tallow fatty alcohols, with oleyl alcohol and with mono-, di- or trialkylphenols and with monoalkyl cyclohexanols containing 6 to 14 carbon atoms in the alkyl radicals are of particular interest. It can be of advantage to use the lowest foaming representatives of this group.

Nonionic surfactants of the type in question include, for example, the commercial products Dehypon® LS 24, LS 36, LS 45, LS 54, LT 24, LT 104, OCP 502 (supplier: Henkel), Dehydol® LT 30 (supplier: Henkel), Lutensol® LF 224, LT 30 (supplier: BASF), Triton® CF 54 and DF 12 (supplier: Rohm & Haas).

The nonionic surfactants are used in quantities of around 3 to 20% by weight and preferably in quantities of around 5 to 10% by weight.

Suitable amphoteric surfactants include derivatives of tertiary aliphatic amines or quaternary aliphatic ammonium compounds, of which the aliphatic radicals may be linear or branched and of which one bears a carboxy, sulfo, phosphono, sulfato or phosphato group. Examples of such amphoteric surfactants are dimethyl tetradecyl glycine, dimethyl hexadecyl glycine, dimethyl octadecyl glycine, 3-(dimethyldodecylammonio)-1-propane sulfonate and the amphoteric surfactants marketed under the names of Dehyton® AB, CB and G (supplier: Henkel). They are used in quantities of around 0 to 10% by weight and preferably in quantities of around 2 to 5% by weight.

In order to guarantee a clear in-use solution and favorable corrosion behavior, even where the disinfectant concentrates according to the invention are used with hot water, the cleaning disinfectants according to the invention may contain complexing agents and corrosion inhibitors, preferably selected from the groups of phosphonic acids, aminocarboxylic acids and salts thereof, more particularly alkali metal salts. Suitable complexing agents are, for example, the alkali metal salts and preferably the sodium salts of methane diphosphonic acid, hydroxyethane-1,1-diphosphonic acid, 1-aminoethane-1,1-diphosphonic acid, aminotri(methylenephosphonic acid), ethylenediamine tetra (methylenephosphonic acid), diethylenetriamine penta (methylenephosphonic acid), 2-phosphonobutane-1,2,4-tricarboxylic acid, nitrilotriacetic acid (NTA), ethylenediamine tetraacetic acid and hydroxyethyl ethylenediamine triacetic acid. NTA is preferred. 1,2,3-Benzotriazole may also be used as a pure corrosion inhibitor. Complexing agents and corrosion inhibitors such as these are preferably present in the disinfectants according to the invention in quantities of not more than 6% by weight and preferably in quantities of around 0.5% by weight to 3% by weight.

In addition, the cleaning disinfectant concentrates according to the invention may contain typical additives, such as dyes or fragrances. Typical additives such as these are preferably present in the disinfectants according to the invention in quantities of not more than 1% by weight.

In addition, the disinfectants according to the invention may contain water-soluble organic solvents, preferably from the groups of alcohols containing 1 to 4 carbon atoms, glycols containing 2 to 4 carbon atoms and the diglycols and diglycol ethers derived therefrom. Solvents of the type in question are, for example, methanol, ethanol, propanol, isopropanol, tert.butanol, ethylene glycol, propylene glycol, butylene glycol, diethylene glycol, dipropylene glycol, diethylene glycol monomethyl ether, diethylene glycol monoethyl ether, diethylene glycol monopropyl ether and diethylene glycol monobutyl ether. Organic solvents may be used in quantities of around 5 to 35% by weight and preferably in quantities of around 10 to 20% by weight. Solvents and solubilizers are preferably present in the disinfectants according to the invention in quantities of not more than 40% by weight and, more preferably, in quantities of around 10% by weight to around 30% by weight.

DE 40 05 784 A1 describes disinfectant concentrates essentially containing 10 to 60% by weight of phenoxyethanol or a mixture of 2-phenoxy-1-propanol and 1-phenoxy-2-propanol, 0.5 to 50% by weight of a guadinium and/or a quaternary ammonium compound, 3 to 25% by weight of a nonionic surfactant and 0.1 to 10% by weight of an organic nitrogen-containing base, such as tetrabis-(2-hydroxypropyl)-N,N',N'-ethylenediamine and their use as a mycobactericide and virucide. The effect of the mixture of phenoxyalkanol and quaternary ammonium compound is said to be enhanced in dependence upon the nitrogen-containing base used. Disclosures such as these are of no relevance to the present invention. By contrast, there is no reference in the prior art to solubility and improvements therein by benzyl alcohol and/or phenoxyalkanols.

EXAMPLES

Various formulations with the following composition:

25% by weight of composition U
5 to 10 % by weight of solvent
0 to 10 % by weight of solubilizer
7% by weight of $C_{12-14}$ alkyl 9EO butyl ether (Dehypon® LS 104 L)
0.5% by weight of 1,2,3-benzotriazole (Preventol® C8-100)
0.2% by weight of NTA balance to 100% by weight water were prepared and cooled in quantities of 100 ml to a temperature of around 0° C. All the samples were cloudy. They were then slowly heated and the onset of the clear point in ° C. was determined. The results are set out in the following Table and illustrate the advantages of the solubilizers added in accordance with the invention.

|  | Alone | | 10% by weight in a ratio of 1:1 | | | | | | |
|---|---|---|---|---|---|---|---|---|---|
|  | 5% by weight | 10% by weight | Butyl diglycol | Ethanol | Isopropanol | Propanol | Phenoxy-propanol | Phenoxy-ethanol | Benzyl alcohol |
| Dimethyl formamide*) | 23 | 23 | — | — | — | — | — | — | — |
| Methyl-2-pyrrolidone | 23 | 23 | — | — | — | — | — | — | — |
| Polydiol | 23 | 23 | — | — | — | — | — | — | — |
| Butanediol | 22 | 22 | — | — | — | — | — | — | — |
| Propylene glycol | 23 | 23 | — | — | — | — | — | — | — |
| Butylene glycol | 23 | 23 | — | — | — | — | — | — | — |
| Glycerol | 21 | 21 | — | — | — | — | — | — | — |
| Butyl diglycol | 15 | 14 | — | 13 | 11 | 11 | 10 | 11 | 11 |
| Ethanol | 15 | 15 | 13 | — | 12 | 11 | 12 | 12 | 11 |
| Isopropanol | 14 | 12 | 11 | 12 | — | 11 | 10 | 11 | 11 |
| Propanol | 14 | 10 | 11 | 11 | 11 | — | 10 | 10 | 9 |
| Phenoxy propanol**) | 15 | 9 | 10 | 12 | 10 | 10 | — | 8 | 3 |
| 1-Phenoxy-ethanol | 15 | 10 | 11 | 12 | 11 | 10 | 8 | — | 7 |
| Benzyl alcohol | 10 | 7 | 11 | 11 | 11 | 9 | 3 | 7 | — |

*)Solvent
**)Solubilizer

We claim:

1. A clear aqueous cleaning and disinfectant composition comprising from about 5% to about 40% by weight of the reaction product of:

(a) an N-substituted propylenediamine corresponding to formula I:

$$R_1-NH-CH_2-CH_2-CH_2-NH_2 \qquad (I)$$

in which $R_1$ is a linear alkyl radical containing 12 to 14 carbon atoms, and (b) a compound corresponding to formula II:

$$R_2-O-CO-CH_2-CH_2-CH(NH_2)-COOH \qquad (II)$$

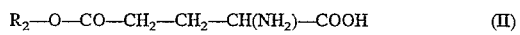

in which $R_2$ is a hydrogen atom or an alkyl radical containing 1 to 4 carbon atoms, in a molar ratio of (a) to (b) of from about 1:1 to about 1:2, respectively, and containing (c) from about 5% to about 35% by weight of an organic water-soluble solvent selected from an alcohol containing 1 to 4 carbon atoms, a glycol containing 2 to 4 carbon atoms and the diglycols and dialycol ethers derived therefrom, and (d) from about 3% to about 30% by weight of a solubilizer selected from the group consisting of benzyl alcohol, 2-phenoxyethanol, 1-phenoxypropanol, and mixtures thereof, based on the weight of said composition.

2. The composition of claim 1 wherein said reaction product of components (a) and (b) is present in an amount of from about 10 to about 25% by weight, based on the weight of said composition.

3. The composition of claim 1 wherein the ratio by weight of said reaction product to said solubilizer is from about 6.0:1.0 to about 0.05: 10, respectively.

4. The composition of claim 1 containing a surfactant selected from the group consisting of nonionic surfactants, amphoteric suffactants, and mixtures thereof.

5. The composition of claim 4 wherein said nonionic surfactants are present in an amount of from 3 to 20% by weight, and said amphoteric surfactants are present in an amount of from 0 to 10% by weight, based on the weight of said composition.

6. The composition of claim 1 wherein said composition has a clear point at a temperature below 20° C.

7. The composition of claim 1 containing from about 0.5 to about 3% by weight of a complexing agent and a corrosion inhibitor, based on the weight of said composition.

8. A process for preparing a clear aqueous cleaning and disinfectant composition comprising adding to said composition:

(a) from about 5% to about 40% by weight of the reaction product of an N-substituted propylenediamine corresponding to formula I:

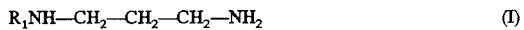

$$R_1NH\text{---}CH_2\text{---}CH_2\text{---}CH_2\text{---}NH_2 \qquad \text{(I)}$$

in which $R_1$ is a linear alkyl radical containing 12 to 14 carbon atoms, and (b) a compound corresponding to formula II:

$$R_2\text{---}O\text{---}CO\text{---}CH_2\text{---}CH_2\text{---}CH(NH_2)\text{---}COOH \qquad \text{(II)}$$

in which $R_2$ is a hydrogen atom or an alkyl radical containing 1 to 4 carbon atoms, in a molar ratio of (a) to (b) of from about 1:1 to about 1:2, respectively, and adding thereto (c) from about 5% to about 35% by weight of an organic water-soluble solvent selected from an alcohol containing 1 to 4 carbon atoms, a glycol containing 2 to 4 carbon atoms and the diglycols and diglycol ethers derived therefrom, and (d) from about 3% to about 30% by weight of a solubilizer selected from the group consisting of benzyl alcohol, 2-phenoxyethanol, 1-phenoxypropanol, and mixtures thereof, based on the weight of said compostion, and (e) the balance, water.

9. The process of claim 8 wherein said reaction product of components (a) and (b) is present in an amount of from about 10 to 25% by weight, based on the weight of said composition.

10. The process of claim 8 wherein the ratio by weight of said reaction product to said solubilizer is from about 6.0:1 to about 0.05: 1.0, respectively.

11. The process of claim 8 further comprising adding a surfactant selected from the group consisting of nonionic surfactants, amphoteric surfactants, and mixtures thereof.

12. The process of claim 11 wherein said nonionic surfactants are present in an amount of from 3 to 20% by weight and said amphoteric surfactants are present in an amount of from 0 to 10% by weight, based on the weight of said composition.

13. The process of claim 8 wherein said composition has a clear point at a temperature below 20° C.

14. The process of claim 8 further comprising adding from about 0.5 to about 3% by weight of a complexing agent and a corrosion inhibitor, based on the weight of said composition.

* * * * *